United States Patent [19]
Lynch et al.

[11] Patent Number: 5,118,606
[45] Date of Patent: Jun. 2, 1992

[54] METHODS FOR DETECTING CELLULAR PATHOLOGY BY ASSAYING SPECTRIN AND SPECTRIN BREAKDOWN PRODUCTS

[75] Inventors: Gary S. Lynch, Irvine; Peter A. Seubert, San Mateo; David D. Eveleth, Jr., Irvine, all of Calif.

[73] Assignee: The Regents of the University of California, Oakland, Calif.

[21] Appl. No.: 558,700

[22] Filed: Jul. 26, 1990

Related U.S. Application Data

[63] Continuation-in-part of Ser. No. 240,154, Sep. 2, 1988, abandoned.

[51] Int. Cl.$^5$ .................. C12Q 1/00; G01N 33/53; G01N 33/566; G01N 24/00
[52] U.S. Cl. .................. 435/7.1; 435/4; 436/501; 436/811; 436/174
[58] Field of Search .............. 435/4, 7; 436/811, 513, 436/828, 518, 524, 501, 174

[56] References Cited

PUBLICATIONS

Siman et al., Brain fodrin: Substrate for calpain I, an endogenous calcium-activated protease, Proc. Natl. Acad. Sci. USA 81:3572-3576 (1984).
Seubert et al., Calmodulin Stimulates the Degradation of Brain Spectrin by Calpain, Synapse 1:20-24 (1987).
Harris et al., Mechanism of cytoskeletal regulation (I): functional differences correlate with antigenic dissimilarity in human brain and erythrocyte spectrin, Biophysica Acta 830:147-158 (1985).
Fox et al., Spectrin is Associated with Membrane-Bound Actin Filaments in Platelets and is Hydrolyzed by the $Ca^{2+}$-Dependent Protease During Platelet Activation, Blood 69:537-545 (1987).
Glenney et al., Erythroid spectrin, brain fodrin, and intestinal brush border proteins (TW-260/240) are related molecules containing a common calmodulin-binding subunit bound to a variant cell type-specific subunit, Proc. Natl. Acad. Sci. USA 79:4002-4005 (1982).
Jonathan Davis and Vann Bennett, Brain Spectrin Isolation of Subunits and Formation of Hybrids with Erythrocyte Spectrin Subunits, The Journal of Biological Chemistry 258:7757-7766 (1983).
Tadashi Yamashita, Changes in Brain Proteins Following Transient Ischemia in Mongolian Gerbils, Dept. of Neuropsychiatry, Osaka Univ. Med. School.
Siman et al., Calpain I Activation is Specifically Related to Excitatory Amino Acid Induction of Hippocampal Damage, The Journal of Neuroscience 9(5):1579-1590 (1989).
Seubert et al., Lesions of entorhinal cortex produce a calpain-mediated degradation of brain spectrin in dentate gyrus, Brain Research 459:226-232 (1988).
Kuwaki et al., Nilvadipine Attenuates Ischemic Degradation of Gerbil Brain Cytoskeletal Proteins, Stroke 20:78-83 (1989).

(List continued on next page.)

Primary Examiner—Robert A. Wax
Assistant Examiner—David R. Preston
Attorney, Agent, or Firm—Pretty, Schroeder, Brueggemann & Clark

[57] ABSTRACT

The invention provides a method for the detection of cellular pathology by means of an immunoassay to determine the presence of stable breakdown products, termed BDP's or BDP1 and BDP2, of the cytoskeleton component spectrin. In one aspect of the invention, the components from a sample of spectrin-containing cells are physically separated, as by exposure to an electric field, in such a way that BDP and spectrin are separated. Antibodies reactive with BDP are then contacted with the separated sample, and their binding to that portion of the sample containing any BDP determined. In another aspect of the invention, an assay, such as an ELISA assay, is performed to detect total spectrin immunoreactivity as an indication of cellular death or degradation.

35 Claims, 9 Drawing Sheets

PUBLICATIONS

Seubert et al., Intrahippocampal Colchicine Injection Results in Spectrin Proteolysis, Neuroscience 31:195-202 (1989).

Seubert et al., Stimulation of NMDA receptors induces proteolysis of spectrin in hippocampus, Brain Research 460:189-194 (1988).

Takashi Murachi, Introcellular Regulatory System Involving Calpain and Calpastatin, Biochemistry International 18:263-294 (1989).

Siman, R. and Noszek, J., Excitatory Amino Acids Activate Calpain I and Induce Structural Protein Breakdown In Vivo, Neuron 1:279-287 (1988).

Groome et al., A new epitope on human myelin basic protein arising from cleavage by a metalloendoprotease associated with brain myelin membranes, Journal of Neuroimmunology 19:77-88 (1988).

Appleyard et al., "Monoclonal Antibodies Detect a Spectrin-Like Protein in Normal and Dystrophic Human Skeletal Muscle", Proc. Natl. Acad. Sci. USA (1984), vol. 81, 776-780.

Arduini et al., "Spectrin Degradation in Intact Red Blood Cells by Phenylhydrazine", Biochemical Pharmacolog. (1985) 4283-4289.

Davis et al., 1983, Brain Spectrin, J. Biol. Chem. 256: 7757-7766.

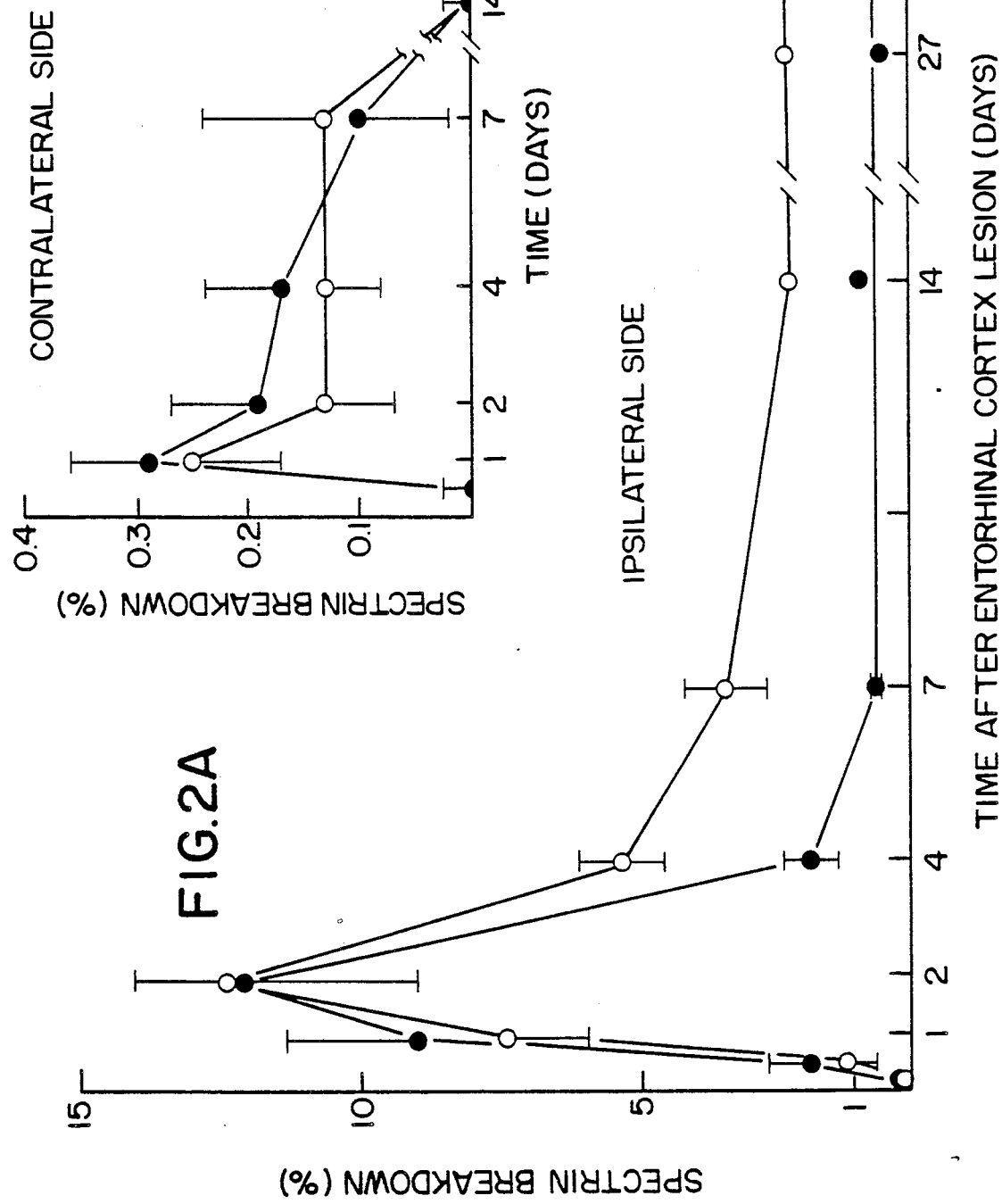

METHODS FOR DETECTING CELLULAR PATHOLOGY BY ASSAYING SPECTRIN AND SPECTRIN BREAKDOWN PRODUCTS

RELATED APPLICATIONS

This is a Continuation/In/Part of parent U.S. Pat. application, Ser. No. 240,154, filed Sept. 2, 1988, inventors Lynch and Seubert, and entitled "Method for Detecting Cellular Pathology," now abandoned.

BACKGROUND OF THE INVENTION

This invention relates to an in vitro method for the detection of cellular pathology, and more specifically to an assay for monitoring cytoskeleton breakdown products to determine cell necrosis.

This invention was made with government support under AFOSR Contract No. 86-0099 (P.I.: Lynch), NIH Grants Nos. NS-18427 and NIA Grant No. AG00538 The government has certain rights in this invention.

The structural integrity of cells is maintained in part by the cytoskeleton, a mesh-like structure composed primarily of proteins, which lies adjacent to the inner cell surface. The cytoskeleton of many cell types (a partial list includes neurons, lymphocytes, kidney, liver, cardiac and smooth muscle, and blood platelets) contain large amounts of a protein either identical to or closely related to brain spectrin (also known as fodrin). Spectrin binds F-actin, and together they are generally associated with the inner face of the cell membrane, where they form a filamentous meshwork.

Brain and many other tissues have been known for some time to express calcium-stimulated proteolytic activity. Studies of degradation in peripheral nerves have indicated that a calcium activated neutral protease, calpain, is critically involved in the degradation of neurofilament proteins following denervation or injury. Two forms of this protease have been identified in brain and other tissues. The two forms are differentiated by their threshold for activation by calcium: calpain I requires micromolar calcium while calpain II is activated by concentrations of calcium between 0 1 and 0.5 mM. The two forms are differentially distributed in the brain. While calpain II is mainly localized in the cytoplasmic fraction of brain cells, the highest activity of calpain I is found in small processes. While the two forms of calpain differ in these and other ways, the term "Calpain" shall be used herein to refer to calcium activated neutral proteases generally, including both forms of calpain.

A variety of cellular insults (e.g., toxins, anoxia, etc.) and disease states (e.g., Alzheimer's, Parkinson's, HIV-induced neuropathy, muscular dystrophy) cause the degeneration and death of cells. Often, however, it is not possible to determine that injury has occurred until degenerative effects are irreversible. There thus exists a need for reliable methods to detect degenerative events as soon as possible, preferably before the onset of pathological symptoms. Preferably such methods also have high sensitivity, wide ranging applicability and ease of administration.

SUMMARY OF THE INVENTION

Briefly, the present invention provides a method of detecting cellular death or degradation in a subject, such as a mammal, comprising analyzing a biological sample from the subject for the presence of spectrin breakdown products and comparing the quantity of spectrin breakdown products to the quantity of spectrin breakdown products in a normal subject, wherein an increased level of spectrin breakdown products indicates cellular death or degradation in the subject. In many cases, the quantity of spectrin breakdown products in the normal subject is substantially undetectable. The biological sample can be any sample from an organism, especially cerebrospinal fluid or a component of blood. The cellular death or degradation detected can, for example, be due to a non-pathological cellular insult, such as a trauma, ischemia, lesions, or exposure to toxins; or may be due to a pathology, including those of the nervous system, such as Alzheimer's disease, Parkinson's disease and muscular dystrophy. Biological samples for the detection of cellular death or degradation in the nervous system can include neural tissue or cerebrospinal fluid.

The step of analyzing the biological sample for the presence of spectrin breakdown products can comprise, for example, contacting a spectrin breakdown product in the sample with a detectably labeled antibody, and can also include the steps of exposing the sample to an electrical gradient so as to separate the components in such a way that spectrin breakdown products are separated from spectrin, contacting the separated components with a detectably labeled antibody that binds to a spectrin breakdown product, and determining the presence of antibody binding, wherein the presence of the antibody binding indicates the presence of spectrin breakdown products. The step of analyzing the biological sample can also comprise the step of staining a separated product with a stain which visualizes the product, and determining the presence of stain binding, wherein the presence of the stain indicates the presence of spectrin breakdown products.

In another embodiment of the invention, a method of detecting cellular death or pathology in a sample from a subject, such as a mammal, is provided comprising obtaining a biological sample from the subject, analyzing the biological sample for the presence of spectrin breakdown products, determining a basal level of spectrin breakdown products, and comparing the determined level to the basal level, wherein a higher level than the basal level indicates cellular death or degradation. The basal level of this method is usually the basal level of spectrin breakdown products in a normal subject, and in many instances can be assumed to be zero. The sample can be any biological sample from the subject, including cerebrospinal fluid, a tissue sample, or blood or any component of blood.

In still another embodiment, there is provided a method of detecting cellular death or degradation in a subject, comprising obtaining a biological sample from the subject; determining the total amount of spectrin, including intact spectrin and spectrin breakdown products, in the sample; determining a basal quantity of the total amount of spectrin; and comparing the determined quantity of the total amount of spectrin to the basal quantity of the total amount of spectrin; wherein a quantity of the total amount of spectrin in the sample greater than the basal quantity indicates cellular death or degradation. The total amount of spectrin can be measured as total spectrin immunoreactivity through such means as an ELISA assay or a Western Blot assay. The sample can be any biological sample from the subject, including cerebrospinal fluid, a tissue sample, or blood or any component of blood.

Another aspect of the present invention provides a method of enriching a biological sample for spectrin breakdown products relative to intact spectrin in a biological sample, comprising precipitating intact spectrin in said sample, leaving spectrin breakdown products in solution in said sample by altering conditions which differentially affect the solubility of the intact spectrin molecule and the spectrin breakdown products; and collecting the precipitated or soluble spectrin breakdown products. The step of precipitating intact spectrin or spectrin breakdown products can comprise altering the pH or ionic strength of the biological sample solution.

Further objects, features and other advantages of the present invention will become apparent from the ensuing detailed description, considered together with the appended figures.

BRIEF DESCRIPTION OF THE FIGURES

FIG. 2 A. Time course of the changes in BDP1 and BDP2 in the ipsilateral side of dentate gyrus following a unilateral entorhinal cortex lesion. B. Time course of the changes in BDP1 and BDP2 in the contralateral side. BDP1 (filled circles) and BDP2 (open circles) levels are expressed as a percentage of the total spectrin immunoreactivity, as determined by scanning relative densitometry.

FIG. 7, Left (rostral to caudal, 1–4) and right (5–8) hippocampi of a control animal and the left (9–12) and right (13–16) hippocampi from a kainate injected animal.

DETAILED DESCRIPTION OF THE PREFERRED EMBODIMENT

Figures 1A, 1B:
FIG. 1 A. Spectrin immunoreactivity in blotted samples of the contralateral (left lane) and ipsilateral (right lane) dentate gyrus two days after a unilateral lesion of the entorhinal cortex. Arrows indicate the alpha and beta spectrin subunits with apparent $M_r$s of about 240 and 230 kilodaltons ("kD"), respectively, and two additional immunoreactive peptides (BDP1 and BDP2) with apparent $M_r$s of about 155 and 150 kD, respectively B. Purified brain spectrin incubated under the following conditions: Lane 1: no additions; Lane 2: 1 mM $CaCl_2$, 1.8 µg/ml calpain I, 10 minutes; Lane 3: 1 mM $CaCl_2$, 3 µg/ml calpain I, 30 minutes; Lane 4: 10 µg of dentate gyrus protein homogenate two days post-lesion; Lane 5; 1 mM $CaCl_2$, 13 µg/ml calpain, 1.25 µg/ml calmodulin, 3 minutes; Lane 6: 1 mM $CaCl_2$, 13 µg/ml calpain, 7.25 µg/ml calmodulin, 30 minutes.

The present invention relates to sensitive and efficient methods for the early detection of cellular death and degradation. The methods of the invention detect cellular death and/or degradation through an assay for spectrin or the breakdown products of spectrin.

The activation of Calpain leads to the proteolysis of many proteins including spectrin. Accordingly, Calpain is believed to cause production of spectrin breakdown products ("BDP's") from spectrin in dead and degenerating cells. Thus, the detection of BDP's is believed to advantageously serve as an indicator of the activation of Calpain.

Spectrin BDP's are unusually stable polypeptides. BDP's can be detected in vivo for up to as long as two months or more after release from the cytoskeleton. Thus, BDP's can advantageously remain to serve as indicators of cellular death or degradation during this period of stability.

There is evidence that the activation of Calpain is an early event in cell death. This is in contrast to other known proteases which are believed to be activated only in the late stages of cell death. The activation of Calpain is believed to often occur before the onset of pathological symptoms associated with cell death. Thus, the detection of BDP's is believed to advantageously be useful as a method for the early detection of cell death, potentially prior to the onset of pathological symptoms.

The present invention advantageously provides a method for the detection of cellular pathology by means of an immunoassay to determine the presence of BDP's of spectrin. Two major BDP's are known, BDP1 and BDP2. In one aspect of the invention, the components from a sample of spectrin-containing cells are physically separated, as by exposure to an electric field, in such a way that BDP's and spectrin are separated. The separated components can then be visualized, as by staining with a stain such as Coomassie Blue. Alternatively, antibodies reactive with BDP's can then be contacted with the separated sample, and antibody binding to the portion of the sample containing BDP's determined. The determined amount of BDP's can then be compared with a basal level of BDP's in similar samples from normal patients. An increase in the level of BDP's is indicative of cellular death or degradation. In many cases, the basal level will be a level which is below the detection threshold of the methods herein described. Thus, in these cases, the detection of any immunoreactivity is an indication of cellular death or degradation.

The invention provides an additional method for the detection of cellular pathology to determine the presence of intact spectrin itself or spectrin immunoreactivity. In one embodiment of this aspect of the invention, an enzyme-linked immunosorbent assay (ELISA) for spectrin immunoreactivity in biological samples, such as tissue extracts, cerebro-spinal fluid (CSF), or blood serum is provided. One particular application of the method is the detection of spectrin or spectrin immunoreactivity in the CSF as an indication of neurodegenerative conditions such as subarachnoid hemorrhage, Alzheimer's Disease, HIV-induced neuropathy and/or stroke.

EXAMPLE I

Identification of Spectrin and BDP's

BDP's were identified from a sample of purified spectrin, by exposing the sample to Calpain for varying lengths of time and exposing the treated samples to SDS-PAGE. Brain spectrin was purified to greater than 90% purity by the method of Davis and Bennett, *J. Biol Chem.* 258:7757-7766 (1983), Which is incorporated herein by reference Calpain was purified to a similar level of purity from rat erythrocyte cytosol according to the method of Seubert, et al., Synapse 1:20-24 (1987), which is incorporated herein by reference.

Spectrin at a concentration of 75 µg/ml was incubated at 30° C. with 100 µM $CaCl_2$, 3 µg/ml calpain I, 20 mM Tris-Cl, 5 mM β-mercaptoethanol and 150 mM NaCl at pH 7.5. Aliquots were withdrawn at 10 minutes and at 30 minutes. The aliquots were added to one-third volume of 3X SDS-PAGE buffer (150mM Tris-$Po_4$, 6%, SDS, 30% glycerol, 3.75 mM EDTA, 3% β-mercaptoethanol, pH 6.8). The samples were heated in a 90° C. water bath for 3-10 minutes, and subjected to SDS-PAGE on 3 to 10% gradient gels. The gels were stained with Coomassie blue and destained with 7% acetic acid. The foregoing method is described in Seubert, et al., Synapse 1:20-24 (1987), which is incorporated herein by reference. The amount of peptide in two peptide bands of approximately 150 kilodaltons (kD) and 155 kD respectively (referred to jointly as the "150 kD bands") were found to increase with exposure time to Calpain. Correspondingly, the amount of peptide in the two peptide bands representing the α and β subunits of spectrin at 240 kD and 230 kD respectively, decreased with exposure time to Calpain. The peptides of the two 150 kD bands were termed BDP1 and BDP2.

Thus, Example I shows that spectrin produces BDP's in the presence of Calpain I. Example I also shows that staining after SDS-PAGE can be used to detect spectrin or BDP's in samples having the relatively high levels necessary for polypeptide bands to be visible to the naked eye upon exposure to stains such as Coomassie Blue. The method of Example I is also well suited to relatively pure samples where the bands corresponding to the BDP's and intact spectrin can be easily identified. Samples having suitably high levels and purity of spectrin and/or BDP's are, for example, obtained from homogenized neural tissues after purification. See Davis and Bennett, supra.

A more sensitive method of detecting spectrin or BDP's, even in complex mixtures of polypeptides can advantageously be obtained by exposing the separated sample to antibodies reactive with spectrin or BDP's. One assay which is suitable for this purpose has come to be known as a Western blot assay.

BDP's exhibit apparent stability towards further degradation, suggesting that antibodies directed against spectrin can recognize the BDP's in biological samples, such as tissues, fluids, etc. Both BDP's and intact spectrin can be recognized by antibodies directed against spectrin. Accordingly, anti-spectrin antibodies will detect both intact spectrin and BDP's when used in a Western blot assay. The following example shows such a Western blot assay, using the gel obtained from Example I and anti-spectrin antibodies to detect the presence of both intact spectrin and BDP's.

EXAMPLE II

Western Blot Assay for Spectrin and BDP's

Antibodies to brain spectrin were raised in rabbits using well known procedures (see, for example, Hurn, B.A.L. and Chantler, S.M., *Meth. Enz.* 10:104-135 (1988), which is incorporated herein by reference). The anti-brain spectrin antibodies were purified from serum by brain spectrinsepharose affinity chromatography. Briefly, antibodies to brain spectrin were isolated from the serum by adsorption to brain spectrin coupled to δ-amino hexanoic acid activated sepharose 4B (Sigma Chemical Co., St. Louis, Mo.). The specifically bound antibodies were then eluted in 0.2 M glycine, pH 2.8. These affinity purified antibodies were then equilibrated to pH 7.4 and frozen until use. The antibodies were found to be reactive against BDP1 and BDP2 as well as to intact spectrin Thus, the 150 kD bands which appeared upon exposure of spectrin to Calpain comprised polypeptides which were cross reactive with spectrin.

Purified brain spectrin was incubated as described in Example I. After SDS-PAGE, the proteins were electrophoretically transferred to a nitro-cellulose membrane using a Trans-Blotter (Bio-Rad, Richmond, Calif.) according to the manufacturer's recommendations for the transfer of high molecular weight proteins. The nitrocellulose sheets were incubated with anti-spectrin antibodies and the bound antibodies detected using an Immuno-Blot assay kit (also available from Bio-Rad) according to the manufacturer's directions. Briefly, anti-rabbit IgG (Bio-Rad, Richmond, Calif.) conjugated to alkaline phosphatase was used in a 5-bromo-4-chloro-3-indolyl phosphate/nitro blue tetrazolium substrate system of detection according to the manufacturer's recommendations. Affinity purified anti-spectrin antibody was diluted 1/750 (in a volume of 50 ml) and incubated overnight with the blot during the primary antibody step. The immunoreactivity of the bands is shown in FIG. 1B, lanes 1-3. Lane 1 shows spectrin without exposure to Calpain; Lane 2 shows spectrin after treatment with 1 mM $CaCl_2$ and 1.8 µg/ml calpain I for 10 minutes; and Lane 3 shows spectrin after treatment with 1 mM $CaCl_2$ and 3 µg/ml calpain I for 30 minutes. It can be seen that in the presence of Calpain, the degradation of spectrin produces BDP's, primarily BDP1 and BDP2.

The findings of Example II and other similar experiments led us to the discovery that the increased Calpain activity following denervation or injury results in significant levels of BDP's being generated in injured tissues.

In accordance with the foregoing discovery, in one aspect of the present invention, there is provided a method for detecting cellular pathology comprising the steps of extracting a sample from a subject mammal and analyzing the sample for the presence of spectrin BDP's. In order to obtain greater sensitivity, the analyzing step can involve an immunoassay using antibodies which recognize spectrin or stable breakdown products of spectrin.

In this aspect of the invention, the amount of BDP's is determined and this amount is compared to a basal level of BDP; an increase of BDP's being indicative of cellular death or degradation. Normally, the basal level is the level of BDP's from healthy cells. The basal level can be taken from a corresponding sample in a healthy subject mammal. Alternatively, the basal level can be obtained from a sample from the same subject at a point in time prior to the insult. Thus, a series of samples can be taken from a single subject over time and analyzed for the presence of BDP's, thereby advantageously providing an indication of the course of cellular death or degradation in the subject. In many samples taken from healthy subjects, the level of BDP's is below the detection threshold of the assays described herein. Accordingly, the basal level against which the detected amount of BDP's are compared is often zero. Therefore, in many samples, the detection of any BDP's is indicative of cellular death or degradation.

The following example illustrates the establishment of a basal level for human CSF.

EXAMPLE III

Establishment of a Basal Level of BDP's in Human CSF

CSF samples are obtained from a healthy human subject. All CSF samples are concentrated by ultrafiltration. Two marker samples are also obtained to identify bands corresponding to intact spectrin and BDP's in completed gels. The first marker sample is a sample of purified spectrin without exposure to Calpain as in Lane 1 of Example I to show the position of intact spectrin. The other marker sample is of purified spectrin after exposure to Calpain as in Lane 3 of Example I to show the position of BDP's. Protein concentration of the samples and marker samples was determined by the method of Bradford, *Anal Biochem.* 72:248-254 (1976), the disclosure of which is hereby incorporated by reference. Ten $\mu g$, of each sample and marker sample is subjected to SDS polyacrylamide gel electrophoresis on a 3-10% gradient gel until a bromophenol marker dye reaches the front of the gel. The proteins are then transferred to nitrocellulose membrane using a transblot apparatus (Bio-Rad, Richmond, Calif.) according to the manufacturer's instructions for high molecular weight proteins. Antibodies are produced as in Example II and used to detect spectrin immunoreactivity on the nitrocellulose membrane Spectrin immunoreactivity is found for each of the CSF samples at positions corresponding to the position of the intact spectrin as determined by the marker sample. However, no detectable spectrin immunoreactivity is found in the CSF samples at a position corresponding to the position of the BDP's determined by the marker sample. Thus, a basal level of BDP's for CSF of this human subject is determined to be zero.

The methods described herein can be used to measure BDP's in a variety of tissues and fluids because spectrin is found in a variety of tissues. For example, BDP's of spectrin have been observed in blood platelets (Fox, et al, Blood 69:537-545 (1987)) and intestinal brush border cells (Glenney, et al., PNAS 79:4002-4005 (1982)). The following tissue taken from rats have been examined by the present inventors and others using the methods described herein and found to exhibit spectrin and BDP's: submandibular gland, brush border, testes, thymus, skeletal muscular, heart muscle, lung, liver, spleen, adrenal gland, kidney, brain. Additionally, humans, gerbils and mice have been determined by the present inventors and others to contain spectrin and BDP's, suggesting that spectrin and BDP's are common to all mammals.

Injury in the mammalian Central Nervous System (CNS) results in both the degeneration of damaged neurons and growth responses of undamaged neuronal elements A well-documented paradigm for investigating the mechanisms underlying these processes involves lesioning the entorhinal cortex, resulting in the production of a well-defined dendritic zone in the dentate gyrus deprived of the majority of its axonal inputs. The anatomical consequences of denervation include dendritic atrophy, glial hypertrophy and atrophy, and a growth response in undamaged axons.

Thus, to show the ability of a preferred method of the present invention to detect the well-defined dendritic zone in the dentate gyrus after lesioning the entorhinal cortex of rats, Examples IV through VIII are provided, showing the detection of cellular death or degradation in the expected tissues.

EXAMPLE IV

Preparation of Dentate Gyrus Sample

Stereotaxically-placed unilateral electrolytic lesions of the entorhinal cortex were made in Sprague-Dawley rats. Animals were sacrificed after postoperative survival times of 0.2, 0.4, 1, 2, 4, 7, 14 and 27 days.

Immediately after sacrificing the animals by decapitation, brains were rapidly dissected in ice-cold homogenization buffer consisting of 0.32 M sucrose, 10 mM Tris, 2 mM EDTA, 1 mM ethylene glycol bis ($\beta$-aminoethylester) N,N,N',N'-tetraacetic acid (EGTA), 100 $\mu$M leupeptin, 1 $\mu$g/ml N-tosyl-L-phenylalanine chloromethyl ketone (TPCK), pH 7.4. Each hippocampus was dissected free and cuts were made with a scalpel blade to isolate the dentate gyrus. With the hippocampus resting on the alvear surface, one cut was made longitudinally along the hippocampal fissure to separate the subiculum and another longitudinal cut removed most of the CA3 field. A third cut was then made in CA1, parallel to the fissure, to remove the majority of CA1. The remaining tissue (10-20 mg) served as the dentate gyrus sample which was used as a tissue sample as in Example V. Contralateral and ipsilateral samples of the dentate gyrus were obtained.

EXAMPLE V

Preparation of Tissue Samples for Electrophoresis

The contralateral dentate gyrus tissue sample and the ipsilateral dentate gyrus tissue sample were each homogenized in 500 $\mu$l of dissection buffer. An aliquot of each was added to one-third volume of 3X SDS-PAGE sample buffer (consisting of 150 mM Tris-PO$_4$, 6% SDS, 30% glycerol, 3.75 mM EDTA, 3% $\beta$-mercaptoethanol, pH 6.8) and placed in a 90° C. water bath for three minutes. The protein concentration of each homogenate was determined by the method of Bradford, supra. The concentration of proteins in each homogenate sample was then adjusted to 0.33 mg/ml with additional sample buffer.

EXAMPLE VI

Separation of Sample Proteins and Transfer to Membranes

Ten $\mu$g of protein from each of the samples from Example V, were subjected to SDS polyacrylamide gel electrophoresis on a 3-10% gradient gel until a bromophenol marker dye reached the front of the gel. The proteins were then transferred to nitrocellulose membrane using a transblot apparatus (Bio-Rad, Richmond, Calif.) according to the manufacturer's instructions for high molecular weight proteins.

EXAMPLE VII

Preparation of Anti-Spectrin Antibodies

Antibodies were produced by the following method: For each rabbit, approximately 200 μg of purified brain spectrin was excised from SDS-polyacrylamide gels (after electrophoretic separation) and emulsified with Freund's complete adjuvant. Multiple subdermal injections were made and the procedure repeated again after two to four weeks, using Freund's incomplete adjuvant. After an additional two weeks, subcutaneous injections of an emulsion containing approximately 100 μg of spectrin were made. This procedure was repeated approximately one month later. Ten days following this series of injections, approximately 20 ml of blood was drawn from each rabbit and the serum collected after allowing the blood to clot overnight at 4° C.

Antibodies to brain spectrin were then affinity purified by adsorption to brain spectrin coupled to δ-amino hexanoic acid activated sepharose 4B, as described in Example II. The affinity purified antibodies were then equilibrated to pH 7.4 and frozen until use.

EXAMPLE VIII

Determination of BDP's Resulting from Brain Lesions

To determine the amount of spectrin immunoreactivity on the membrane of Example VI, the membrane was exposed to the antibody of Example VII as part of a Western Blot assay. Procedures for blocking, primary and secondary antibody incubations and color development were as described in Example II. Quantitation of the immunoreactive species was made using a soft laser scanning densitometer (Model #SLR504-XL, BioMed Instruments, Fullerton, Calif.). An integrator (Model 4270, Varian, Sunnyvale, Calif.) summed the amount of reaction product in each band and expressed them as a percentage of the total in that sample.

The anti-spectrin reactive species present in the contralateral (lane 1) and ipsilateral dentate gyrus (lane 2) two days after a unilateral entorhinal lesion are shown in FIG. 1A. The homogenates of the ipsilateral dentate gyrus exhibited a marked increase in the amount of two peptides, termed BDP1 and BDP2, with apparent $M_r$s of about 155,000 and 150,000 Daltons, respectively.

The procedures of Examples IV through VIII were repeated, allowing various lengths of time to elapse between the lesion and sacrifice of the animals of Example IV. The time course of the changes in BDP1 and BDP2 in the dentate gyrus following a unilateral entorhinal cortex lesion is shown in FIG. 2. BDP's are usually below the limit of detection in samples from unoperated animals. A significant elevation of BDP's in the ipsilateral sample is evident as early as four hours post-lesion. The increase is maximal two days after the lesion, where the BDP's represent 25% of the total immunoreactivity. Two and even four weeks after the lesion, the amounts of BDP's were still significantly increased; the contralateral dentate gyri at two and four weeks showed no detectable BDP's and average BDP2 levels were less than 0.1% of total spectrin immunoreactivity. Small increases in the amounts of BDP's were observed in the contralateral region during the first week following the lesion as compared to non-operated animals.

The results indicate that removal of the main input to the dentate gyrus is followed by a rapid and long-lasting increased degradation of the cytoskeletal protein brain spectrin. It is known that aberrations in cytoplasmic calcium levels occur in the dendritic zone of the dentate gyrus after lesioning. See, for example, Baudry, et al., *J. Neurosci.*, 3:252-259 (1983), the disclosure of which is hereby incorporated by reference. Thus, we believe that the elevated levels of BDP's in these tissues is the result of the activation of Calpain in these tissues by these aberrant levels of calcium. The results of Example VIII, therefore, confirm the ability of the present invention to detect the well-defined dendritic zone in the dentate gyrus after lesioning of the entorhinal cortex in rats.

Examples IX through XI are provided in order to show that the methods utilized in Examples V through VIII have widespread utility in detecting cellular death or degradation. These examples show the detection of cellular death or degradation from a variety of causes and in a variety of cellular tissues through methods of the present invention. As such, these examples are intended to illustrate, not to limit the invention. While the procedures described herein, such as those of Examples V through VIII, are typical of those that might be used, other alternative procedures known to those skilled in the art can be alternatively employed.

EXAMPLE IX

Assay for BDP in the Brindled Mouse, A Hereditary Degenerative Condition

Figure 3:
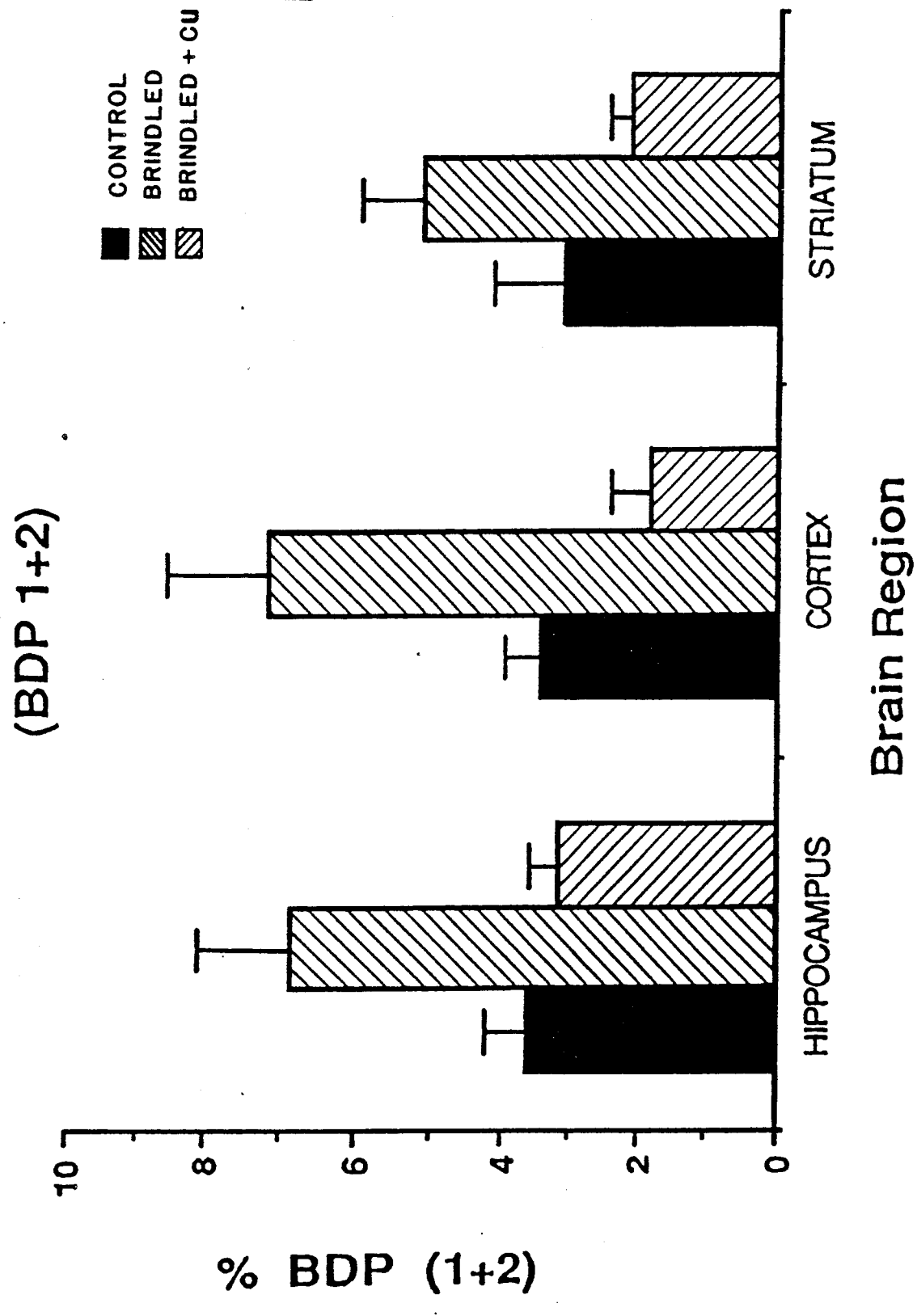
FIGS. 3. Levels of BDP's in regions of the brain of control and Brindled mice, showing the effect of treatment with copper.

Samples from the hippocampus, cortex and striatum of 12 day mouse pups were processed as described for the dentate gyrus samples in Examples V-VIII. The experimental groups were control mice, Brindled mice, and Brindled mice receiving supplemental copper, a treatment which prevents the premature death which otherwise occurs. Brindled mice are characterized in that they have a copper deficit which untreated causes normal degradation. As can be seen in FIG. 3, spectrin BDP's are elevated in the pathological condition and this elevation is blocked by the copper supplement.

EXAMPLE X

Assay for BDP after Exposure to the Industrial Toxin Trimethyltin (TMT)

Figure 4:
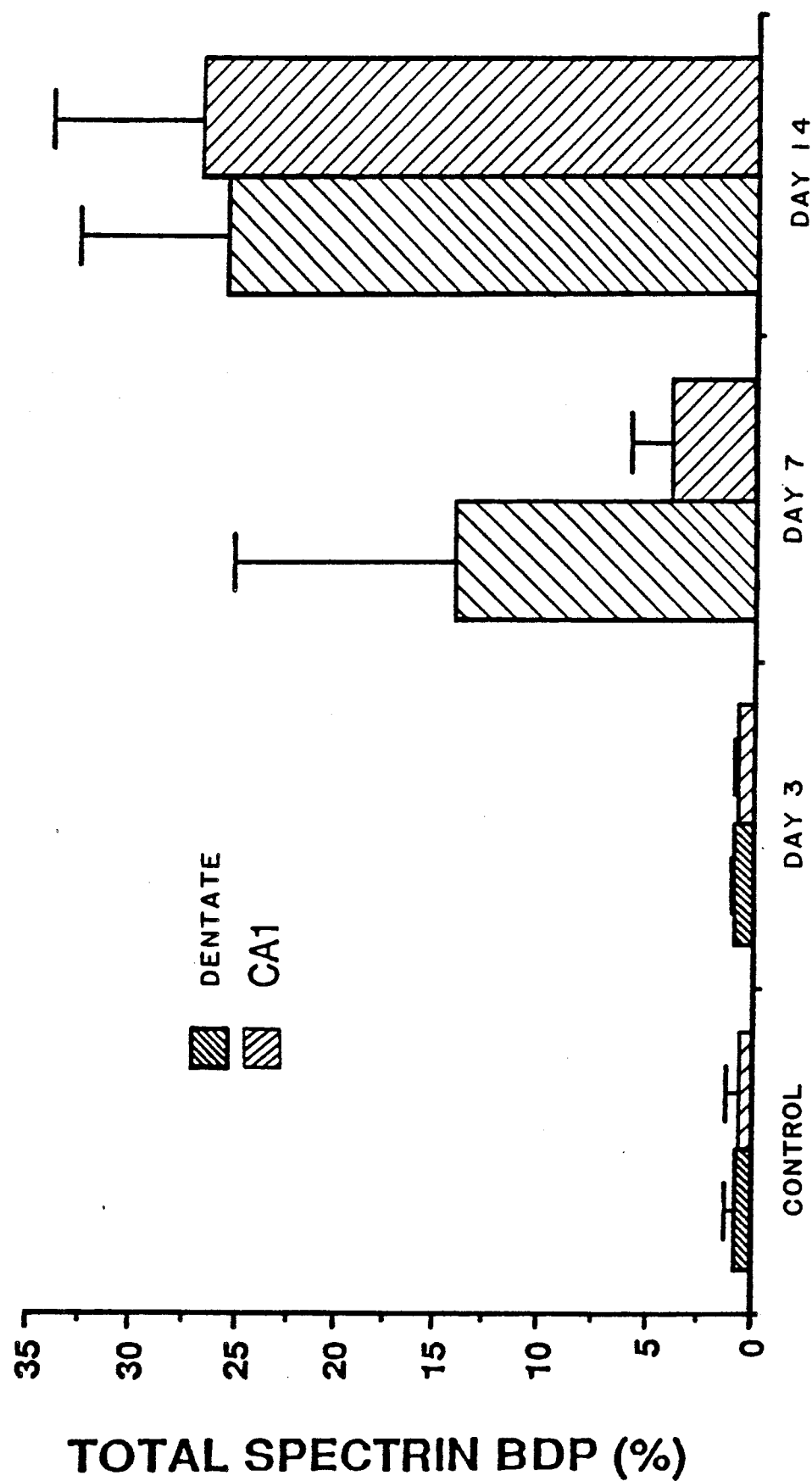
FIG. 4. Levels of BDP's in the dentate gyrus and the CA1 region of the hippocampus of rats receiving trimethyltin.

Three rats were injected intraparitoneally (i.p.) with 10 mg TMT/kg body weight. A fourth rat was injected i.p. with saline alone to serve as control. At 3, 7 and 14 days post-treatment, the dentate gyrus and CA1 regions of the hippocampus of the three test rats were removed and analyzed for BDP's, as described in Examples V-VII. Massive increases in BDP's were noted in both the dentate gyrus and CA1 regions, as depicted in FIG. 4. These regions of the brain have been identified as the regions most at risk to TMT toxin (see Balabin, et al., *Neurosa* 26:337-361 (1988), which is incorporated herein by reference).

EXAMPLE XI

Assay for BDP Following Ischemia

Figure 5:
FIG. 5. Levels of BDP's in the dentate gyrus and the CA1 region of the hippocampus from a gerbil following ischemia.

Carotid arteries were clamped for 10 minutes to interrupt the principal blood flow to the cortex in each of two groups of eight Mongolian gerbils. Two control groups of gerbils were also analyzed. Samples of the CA1 hippocampal region and the cerebellum were taken at 4 hours after ischemia from one group of control gerbils and one group of test gerbils. Samples were also taken at 24 hours after ischemia from the second control and test groups of gerbils. The test gerbils showed elevated BDP's in the CA1 region compared to control animals, as shown in FIG. 5. The blood supply to the cerebellum was not interrupted and this structure showed no such increase. Analysis of BDP levels was as described in Example V–VIII.

Thus, the foregoing examples show that the methods of the present invention can advantageously be used to detect cellular death or degradation from a variety of causes in a variety of samples.

The present invention advantageously provides an additional method for the detection of cellular pathology without the necessity of separating the sample into BDP and intact spectrin. This additional method is by means of an immunoassay to determine the presence of intact spectrin itself or spectrin immunoreactivity regardless of source. Therefore, in this embodiment of the invention, total spectrin immunoreactivity, including immunoreactivity to spectrin and to BDP's, can be measured. In one embodiment of this aspect of the invention, an enzyme-linked immunosorbent assay (ELISA) for spectrin immunoreactivity in biological samples, such as tissue extracts, cerebrospinal fluid (CSF), or blood serum is provided.

In preparation for the competitive ELISA assay of a preferred embodiment, a spectrin sample is immobilized to polystyrene microliter plates. We have found that spectrin desorbs from conventional activated polystyrene plates after immobilization, resulting in an unexpected bell-shaped relationship between the amount of antibody bound and the amount of spectrin in the sample which is measured. While not wishing to be bound by any particular explanation for this unexpected result, it is believed that the desorbed spectrin forms polymers with still immobilized spectrin in the presence of accessory proteins present in the sample. The spectrin polymers are believed to be more accessible to binding of anti-spectrin antibody. In addition, spectrin in the sample is believed to bind to the plate through further polymerization of the spectrin.

In order to prevent the unexpected relationship between the amount of antibody bound and the spectrin in the sample, polystyrene plates can be treated with glutaraldehyde prior to the immobilization of spectrin to the plates. Glutaraldehyde forms covalent bonds to both the polystyrene of the plates and to the spectrin molecules. The use of buffers with conditions, including salinity and pH, unfavorable to the polymerization of spectrin has also been found to prevent the unexpected results. High ion concentration has been found to inhibit formation of spectrin polymers, however, such concentrations also interfere with immunoreactivity. Addition of various other agents has also been found to prevent the unexpected results, including EGTA, sucrose and detergents. Thus, in a preferred method of the present invention, buffers with a pH slightly greater than 7.0 in physiological saline with EGTA, sucrose and detergent is used. Chaotropic salts, such as NaBr or KI, can also be used to inhibit formation of polymers.

When an unknown sample is tested, a limiting amount of anti-spectrin antibody is added to each well along with the sample. Spectrin in the sample competes for antibody with the spectrin immobilized to the plate. Thus, the more spectrin in the sample, the less antibody will bind to the spectrin immobilized to the plate. Accordingly, the amount of antibody binding to the spectrin on the plate provides an indication of the amount of spectrin in the sample. The amount of antibody can be detected by a colorimetric reaction as in a standard ELISA procedure, or can be detected in any known manner, such as through a radioimmune assay.

EXAMPLE XII

ELISA Assay for Spectrin

A spectrin preparation was prepared from rat brains by the method of Davis and Bennett (J. Biol. Chem. 258:7757–7766, 1983). Antibodies to spectrin were prepared by subjecting the spectrin preparation to SDS-PAGE (see Seubert, et al., Synapse 1:20–34, 1987), excising the region of the gel containing the spectrin, homogenizing the gel and immunizing rabbits with the homogenized gel according to established procedures (see, e.g., Hurn and Chantler, Methods Enzymol. 70:104–135, 1980).

Microtiter plates having immobilized spectrin were prepared by first treating microtiter plates (unmodified polystyrene, such as those sold under the trade mark "Corning Easy-Wash") with glutaraldehyde 0.2% in 0.1 M sodium phosphate pH=5.0 for 4 hours at room temperature. After removal of glutaraldehyde, 100 $\mu$l of a solution of spectrin (10 $\mu$g/ml) in 0.1 M sodium phosphate pH=8.0 was added to each well and the plates incubated an additional 4 hours at room temperature. The plates were rinsed with 0.1 M lysine in 0.1M sodium phosphate pH=8.0, and 100 $\mu$l of this lysine solution was added to each well. The plates were then incubated for 4 hours at room temperature. Lysine serves to react with unreacted glutaraldehyde binding sites to prevent the further binding of spectrin to the plates.

For the measurement of spectrin immunoreactivity of an unknown, the lysine solution in each well was discarded and a sample of the unknown was placed in each well. The volume was then adjusted to 50 $\mu$l with 20 mM Tris, 0.8% NaCl, 0.02% KCl, 0.5% bovine serum albumin, 0.05% Tween 20, 2 mM EGTA, 0.2% sodium azide pH=7.2 ("assay buffer"). To this was added 50 $\mu$l of a 1:50,000 dilution of anti-spectrin antiserum in assay buffer. The plates were mixed and incubated overnight at 4° C. The plates were then rinsed 4 times in 10 mM Tris, 0.9% NaCl pH=7.2 ("rinse buffer") and 100 $\mu$l of biotinylated goat anti-rabbit antiserum (available from Vector Laboratories), diluted in assay buffer at the concentration recommended by the manufacturer was added and the plates incubated on a rocking platform at room temperature for 4 hr. The plates were rinsed 4 times with rinse buffer and 100 $\mu$l of ABC (alkaline phosphatase) reagent (also available from Vector Laboratories) prepared according to the manufacturer's instructions in assay buffer was added. The plates were incubated for 2 hrs on a rocking platform at room temperature and rinsed 6 times with rinse buffer. Color was developed by adding 100 $\mu$l of alkaline phosphatase substrate solution (available from Bio-Rad) made according to the manufacturer's directions and incubating for 30 minutes to 4 hours at room temperature.

In parallel with the measurements of the unknown samples, measurements of spectrin immunoreactivity of wells initially containing known concentrations of spectrin were also performed.

Figure 6:
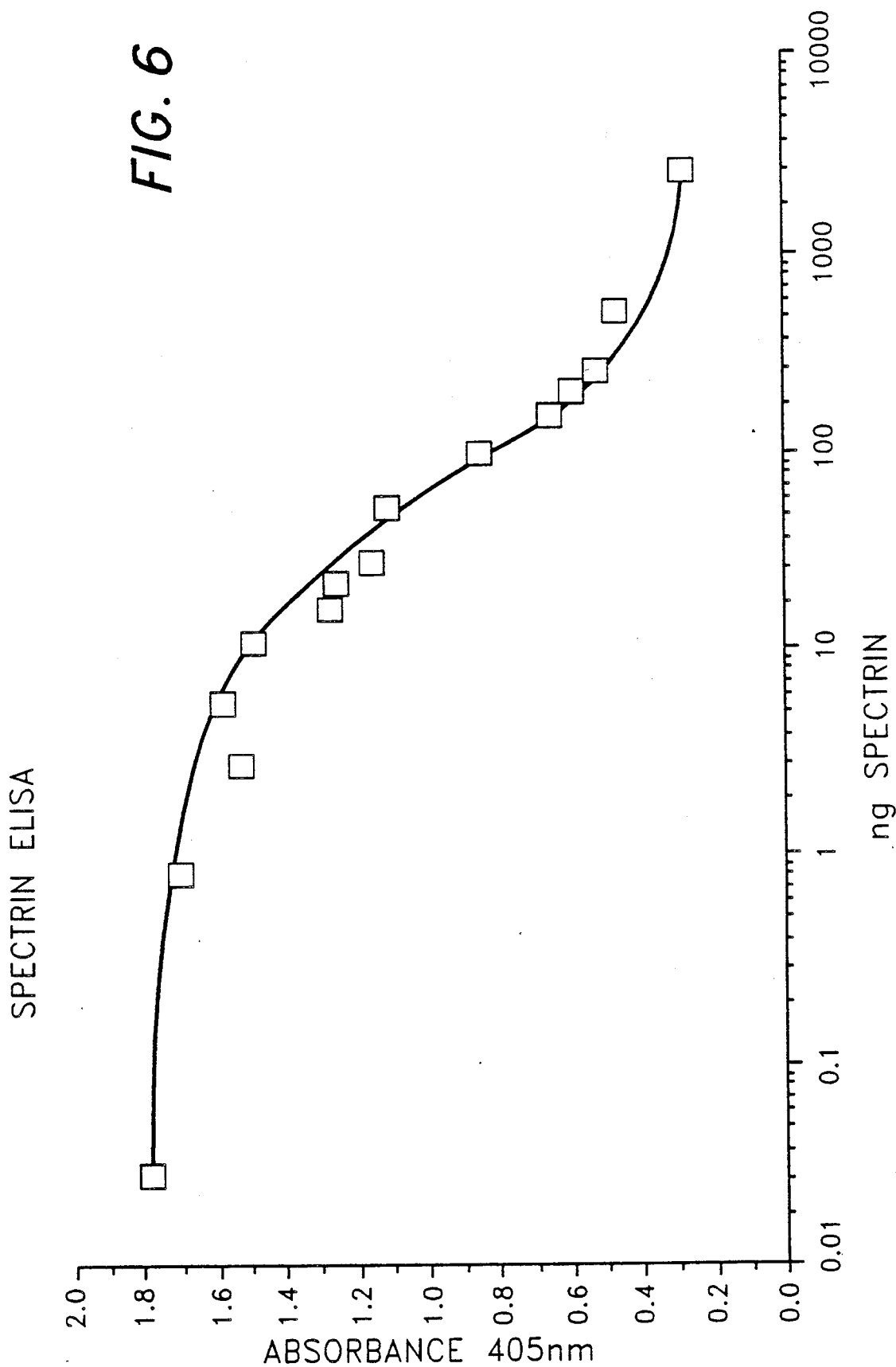
FIG. 6. Standard curve showing absorbance at 405 nm for various levels of spectrin in an ELISA assay.

The absorbance at 405 nm of the wells containing these standard concentrations was read using a plate reader and the standard curve shown in FIG. 6 was produced from this data.

The absorbance at 405 nm of the wells containing unknown samples was also read and the concentration of spectrin determined by comparing the absorbance of the unknown wells to the standard curve. The concentration of spectrin immunoreactivity correlates well with measurements of the same samples which are subjected to the Western Blot assay of Example VIII. The following example demonstrates the correlation between the Western blot and the ELISA assay in neurodegenerating rats.

EXAMPLE XIII

Comparison of Western Assay and ELISA Assay

Adult rats were given intracerebral ventricle injections of 75 ng of kainate, a compound known to cause neurodegeneration within the hippocampus. A second set of rats were given equal volume injections of saline. The rats were allowed to recover for four days. The hippocampi were then removed and divided into four sections, rostral to caudal. Each section was analyzed using both the Western blot assay as in Example II, and using the ELISA assay of Example XII. Results are shown in FIG. 7.

Figure 7A:
FIG. 7A shows the results of the Western blot assay.
Figure 7B:
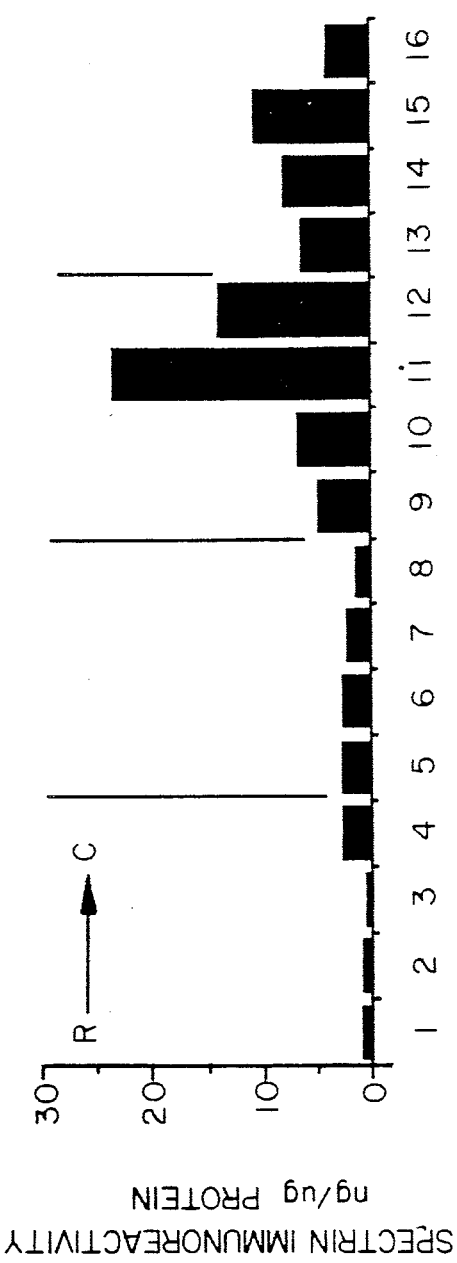
FIG. 7B shows the results of the ELISA assay.

FIG. 7 shows the left (rostral to caudal, 1–4) and right (5–8) hippocampi of a control animal and the left (9–12) and right (13–16) hippocampi from a kainate injected animal. The top panel shows the Western Assay and the bottom panel shows the ELISA assay. It can be seen that the increase in the total amount of immunoreactivity measured by the ELISA correlates well with the increase in BDP's measured by the Western Blot assay.

One particular application of the ELISA of the present invention is the detection of spectrin or spectrin immunoreactivity in the cerebrospinal fluid (CSF) as an indication of neurodegenerative conditions, including subarachnoid hemorrhage, stroke, multiple infarction dementia, HIV-induced neuropathy and Alzheimer's Disease.

Although it is possible to detect small quantities of spectrin in normal CSF concentrated by ultrafiltration; in normal unconcentrated CSF, virtually no spectrin immunoreactivity is detected using the ELISA assay of the present invention. Therefore, the detection of either spectrin or spectrin BDP's in unconcentrated CSF would be indicative of cellular death or degradation within the nervous system. Although spectrin is present in isodermal cells lining the ventriculus and in particular in specific cells standing between the CSF and the blood, the number of such cells is very small compared to neural cells. The death or degradation of glial cells, the support cells for neurons, would also be capable of contributing spectrin or BDP's to the CSF. However, after death or degradation of glial cells, the death or degradation of the neural cells such cells support would follow shortly thereafter. Therefore, the vast majority of spectrin immunoreactivity found in the CSF would be indicative of breakdown of neural cells.

The cerebrospinal fluid of humans can be assayed either directly or after concentration using lyophilization or centrifugal ultrafiltration (using materials such as those sold under the trademarks "Centricon-10" or "Amicon"). The following example illustrates one typical method of the present invention for assaying human CSF for the presence of spectrin immunoreactivity.

EXAMPLE XIV

Assay of Spectrin Immunoreactivity in Human CSF

Figure 8:
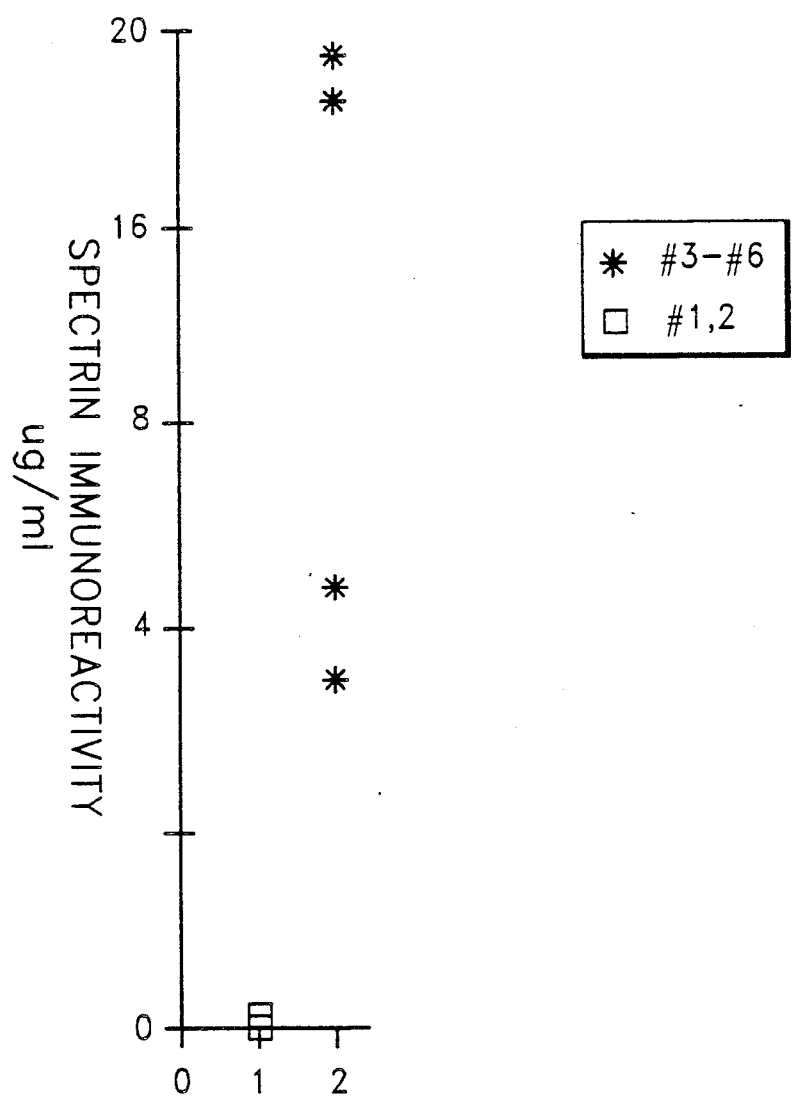
FIG. 8. Spectrin immunoreactivity of CSF samples, as measured by ELISA, from two patients of group 1 (unruptured aneurisms) and four patients of group 2 (ruptured aneurisms).

Cerebrospinal fluid samples were obtained from 2 patients diagnosed as having unruptured aneurysms (group 1) and from 4 patients in which the aneurysm has burst producing subarachnoid hemorrhage (group 2). Two ml of each sample was lyophilized, resuspended in 100 µl water, and 10 µl of the resulting solution was analyzed for spectrin immunoreactivity using the ELISA assay of Example XII. Results are shown in FIG. 8. The CSF samples from the subarachnoid hemorrhage group all showed spectrin immunoreactivity while the unruptured aneurism group had no detectable spectrin immunoreactivity.

Thus, it can be seen from Example XIV that the presence of detectable quantities of spectrin immunoreactivity in the CSF is indicative of cellular death or degeneration in neural tissue.

In summary, the foregoing examples clearly show that neurodegeneration in vivo dramatically elevates total spectrin immunoreactivity, as measured by the ELISA. To demonstrate the widespread applicability of the ELISA assay in detecting neurodegeneration, the following example was performed.

EXAMPLE XV

Levels of Spectrin Immunoreactivity in CSF

Figure 9:
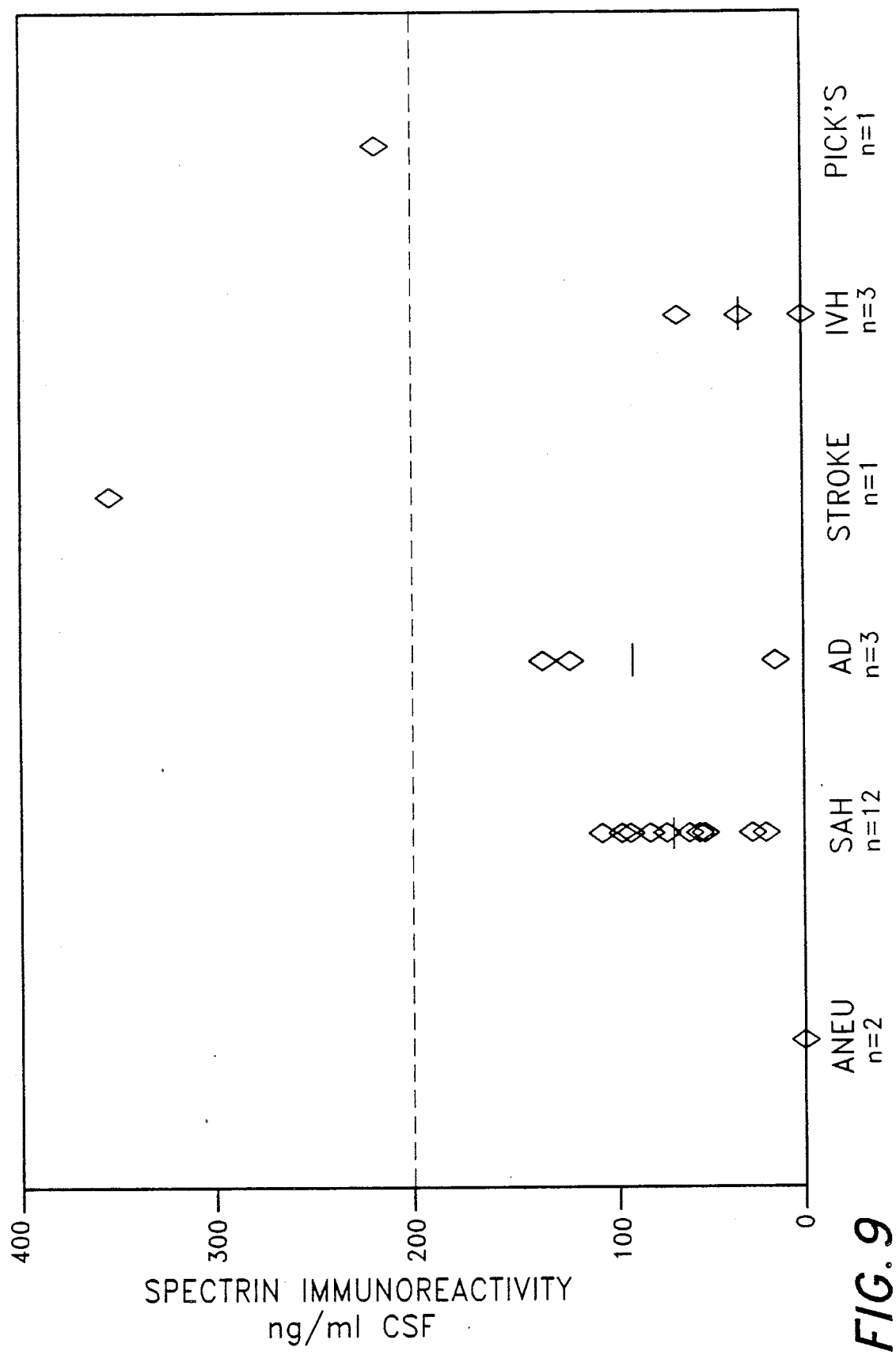
FIG. 9. Spectrin immunoreactivity of CSF samples, as measured by ELISA for: ANEU (unruptured aneurism patients (n=2)); SAH (subarachnoid hemorrhage patients (n=12)); AD (Alzheimer's Disease patients (n=3)); STROKE (stroke patient (n=1)); IVH (intravascular hemorrhage patients (n =3)); and PICK'S (Pick's Disease Patient (n=1)).

Total spectrin immunoreactivity was measured, using the ELISA method of Example XII, in CSF taken from a number of different patients suffering from a variety of conditions known to be associated with neurodegeneration. Results are shown in FIG. 9. The first column of FIG. 9, labeled "ANEU" shows the results of two patients who had brain aneurysms detected and surgically corrected before the aneurisms burst, as in Group 1 of Example XIV. Thus, significant neurodegeneration would not be expected in these patients. As can be seen in FIG. 9, no spectrin immunoreactivity was found in CSF taken from these patients. The data confirms that no spectrin immunoreactivity is detected in CSF in non-neurodegenerating mammals using the ELISA assay of the present invention.

The next column of FIG. 9, labeled "SAH", shows spectrin immunoreactivity measurements in CSF of 12 patients with subarachnoid hemorrhage who had had CSF drains installed. The CSF from all 12 patients shows spectrin immunoreactivity, indicating that neurodegeneration has occurred.

The third column of FIG. 9, labeled "AD" shows spectrin immunoreactivity measurements in CSF from 3 Alzheimer's disease sufferers. All three patients show spectrin immunoreactivity in their CSF, indicating neurodegeneration has occurred.

The fourth column of FIG. 9 shows spectrin immunoreactivity in the CSF from one stroke victim. It can be seen that spectrin immunoreactivity is quite high in this patient, indicating significant neurodegeneration.

The fifth column of FIG. 9, labeled "IVH" shows spectrin immunoreactivity from three premature infants suffering from intraventricular hemorrhage. Results show that two out of three of these patients show spectrin immunoreactivity in their CSF, indicating neurodegeneration.

The last column of FIG. 9 shows spectrin immunoreactivity in one victim of Pick's disease. The results show high levels of spectrin immunoreactivity in this patient, indicative of the neurodegeneration which accompanies this disease Pick's disease is clinically very difficult to distinguish from Alzheimer's disease. Presently, Pick's can only be readily distinguished from Alzheimer's upon autopsy. It can be seen from the present data, that the Pick's sufferer had significantly higher levels of spectrin immunoreactivity than any of the Alzheimer's sufferers. Thus, it is believed that the present method will provide a diagnostic tool in distinguishing between these two diseases by the generally higher levels of spectrin immunoreactivity found in the CSF of Pick's patients.

Thus, it can be seen from the foregoing example that measurements of spectrin immunoreactivity in CSF are useful indicators of neurodegeneration from a wide spectrum of clinical causes.

The spectrin immunoreactivity detected in all of the foregoing examples is, of course, due to a large number of different antigenic epitopes. It is believed that after the proteolysis of spectrin to BDP's, additional or occult epitopes are exposed which are not present in intact spectrin. Thus, when performing the ELISA assay using polyclonal antibodies raised against BDP's, BDP's can give a stronger signal than the intact spectrin. In such assays, treating the spectrin in such a way to expose the occult epitopes, can also give a stronger signal than intact spectrin.

The anti-spectrin antibodies used in the Western Blot assays of examples II-XI, were affinity purified using the affinity purification method described in Example II. This affinity purification step with intact spectrin, resulted in the purification of antibodies to epitopes of spectrin present and exposed in intact spectrin. However, the raw serum contained at least two other classes of antibodies which react against spectrum. One class of antibodies are to epitopes of spectrin not exposed in the intact tetrameres, but exposed in cleaved spectrin. Another class of antibodies would be antibodies specific to spectrin-SDS complexes. This class of antibodies is expected because the spectrin used to immunize the rabbits producing the antibodies in Example II was purified from SDS-PAGE, resulting in the formation of these SDS-spectrin complexes. In order to demonstrate that raw, not affinity purified, anti-spectrin antibodies raised against denatured rat spectrin react more efficiently with denatured spectrin than with intact spectrin, and that, therefore, occult epitopes exist and that antibodies against the occult epitopes can be used to distinguish native from denatured spectrin, the following example was performed.

EXAMPLE XVI

Immunoreactivity of Denatured and Native Spectrin

Spectrin was immobilized onto polystyrene plates as in Example XII. Each well was incubated with one of four denaturing treatments for one hour at room temperature and then washed six times in wash buffer (50mM tris, 150 mM NaCl pH=7.5). The four treatments were: control (wash buffer), 1% SDS, 1 M acetic acid, and 1 M KI. Four wells for each treatment were analyzed. The amount of spectrin immunoreactivity on the plate was determined by incubating plates with raw serum from immunized rabbits at 1:10,000 dilution in assay buffer (100 μl well) overnight at 4° C., rinsing the plates four times with wash buffer, and detecting bound antibody using the Vector ABC-AP kit as in Example XII. Results are shown in Table 1.

TABLE 1

| TREATMENT | ABSORBANCE (405 nm) ± S.D. |
|---|---|
| Control | 0.997 ± 0.115 |
| 1% SDS | 2.540 ± 0.281 |
| 1M Acetic Acid | 1.110 ± 0.087 |

TABLE 1-continued

| TREATMENT | ABSORBANCE (405 nm) ± S.D. |
|---|---|
| 1M KI | 1.835 ± 0.117 |

It can be seen from the results of Table 1, that raw serum from rabbits immunized with SDS-treated spectrin recognizes denatured spectrin more effectively than the native, control-treated spectrin. Not unexpectedly, the SDS-treated spectrin reacts the most strongly with this serum. Thus, it is clear from these results that denaturing spectrin exposes occult epitopes not present in intact spectrin molecules. It is expected that other denaturing treatments, such as TCA, organic solvents, ethanol and guanidine, will produce similar increases in immunoreactivity.

It is also believed that the cleavage of intact spectrin into BDP's exposes hidden epitopes. In order to demonstrate that cleavage of spectrin in solution exposes hidden epitopes and that antibodies directed against these epitopes can be used to distinguish intact spectrin from cleaved spectrin, the following example was performed.

EXAMPLE XVII

Cleavage of Spectrin to Increase Immunoreactivity

Rat brain was homogenized in 10 mM HEPES, 1 mM EGTA, 1 mM DTT pH=7.2. The homogenate was centrifuged at 12,000 ×g for ten minutes and the supernatant split into two fractions. $CaCl_2$ was added to Fraction 2 in order to activate Calpain. The final concentration of $Ca^{++}$ in Fraction 2 was 50 mM. No $CaCl_2$ was added to Fraction 1. Both fractions were incubated at 37° C. for 30 minutes. The immunoreactivity of the samples was taken both before and after this incubation period using the ELISA assay of Example XII. Extensive proteolysis of the second sample, leading to formation of BDP's, was confirmed by Western Blot analysis as in Example II. No proteolysis was detected in any of the other samples No precipitate was observed in any samples Results of the ELISA determination are shown in Table 2.

TABLE 2

| FRACTION | ABSORBANCE AT 405 nm | |
|---|---|---|
| | t = 0 min. | t = 30 min. |
| 1 (−$Ca^{++}$) | 0.316 ± 0.014 | 0.381 ± 0.023 |
| 2 (+$Ca^{++}$) | 0.334 ± 0.033 | 0.451 ± 0.022 |

It can be seen from Table 2 that in Fraction 2 where Calpain is activated that total immunoreactivity increased from an average of 0.381 to an average of 0.451, an increase of 18%. In no instance did the immunoreactivity of Fraction 1 exceed the immunoreactivity of Fraction 2. Thus, the foregoing example shows that cleavage of spectrin into BDP's in vitro increases the immunoreactivity towards raw serum of rabbits immunized with SDS-spectrin complexes.

Referring back to FIG. 7, where the Western Blot assay is compared to the ELISA assay, it can be seen that the amount of spectrin immunoreactivity is most dramatically increased in those sections of rat hippocampus in which increased BDP's are found. Thus, the data of FIG. 7 confirms that immunoreactivity is enhanced by cleavage into BDP's in vivo, as well as in vitro.

The availability of hidden epitopes in intact spectrin suggests an ELISA assay or other immunoassay for specifically detecting BDP's as opposed to intact spectrin. Such an assay could use antibodies directed solely to these hidden epitopes, obtained through methods known in the art, such as through affinity purification or the production of a monoclonal antibody directed to a hidden epitope. It is expected that the affinity purification of the class of antibodies directed to epitopes present and exposed in intact spectrin as in Example II results in a fraction not bound to the spectrin-sepharose containing antibodies directed to hidden epitopes.

Using a source of antibodies directed to hidden epitopes, it is expected that a determination of the amount of total spectrin immunoreactivity and the amount of BDP immunoreactivity could be separately made.

Alternatively, it is believed to be possible to separate intact spectrin from BDP's, including the BDP1 and BDP2 polypeptides visualized by Western blot and other spectrin fragments, by altering the conditions of the solution to affect the solubility of the intact spectrin molecule. By altering the pH, ionic strength, or other such factors, it is believed possible to solubilize the BDP's while precipitating the intact spectrin molecules. It is believed that treatment of samples containing spectrin immunoreactivity with an agent selected from the group consisting of detergents, agents which produce an acidic or basic pH (preferably a pH of greater than 8.5 or less than 5.5), chaotropic agents and organic solvents of lowered dielectric will result in the altered solubility conditions required to precipitate intact spectrin without precipitating some or all of the BDP's. By removing the precipitated intact spectrin molecules, a determination of the amount of BDP's present can be obtained. For commercial utility, an enrichment for BDP's of at least ten fold is preferable, more preferably on the order of one hundred fold.

Although the invention has been described with reference to the presently preferred embodiments, it should be understood that various modifications can be made without departing from the spirit of the invention. Accordingly, the invention is limited only by the following claims.

We claim:

1. A method of detecting cellular death or degradation in a subject, comprising:
    analyzing a biological sample from the subject for the presence of spectrin breakdown products;
    comparing the quantity of spectrin breakdown products to the quantity of spectrin breakdown products in a normal subject, wherein an increased level of spectrin breakdown product indicated cellular death or degradation in the tissues from which the sample is taken or in tissues in fluid communication with the sample.

2. The method of claim 1, wherein the quantity of spectrin breakdown products in the normal subject is substantially undetectable when determined by the method used in the analyzing step.

3. The method of claim 1, wherein the biological sample comprises cellular tissue from a mammal and wherein the cellular death or degradation has occurred among the cells of the sample.

4. The method of claim 1, wherein the biological sample is selected from the group consisting of cerebrospinal fluid and a component of blood.

5. The method of claim 1, wherein the cellular death or degradation results from a non-pathological cellular insult.

6. A method of claim 5, wherein the cellular insult is selected from the group consisting of a trauma, ischemia, lesions, and exposure to toxins.

7. A method of claim 5, wherein the cellular insult is to the nervous system, and wherein the biological sample comprises neural tissue or cerebrospinal fluid.

8. The method of claim 1, wherein the cellular death or degradation results from a pathological condition.

9. The method of claim 8, wherein the pathological condition is a pathological condition affecting the nervous system.

10. The method of claim 9, wherein the pathology is selected from the group consisting of Alzheimer's disease, Parkinson's disease and muscular dystrophy, and wherein the biological sample is neural tissue or cerebrospinal fluid.

11. The method of claim 1, wherein the step of analyzing the biological sample for the presence of spectrin breakdown products comprises contacting a spectrin breakdown product in the sample with a detectably labeled antibody.

12. The method of claim 1, wherein the step of analyzing the biological sample comprises the steps of:
    a. exposing the sample to an electrical gradient so as to separate the components in such a way that spectrin breakdown products are separated from spectrin;
    b. contacting the separated components with a detectably labeled antibody that binds to a spectrin breakdown product; and
    c. determining the presence of antibody binding, wherein the presence of the antibody binding indicates the presence of spectrin breakdown products.

13. A method of claim 1, wherein the step of analyzing the biological sample comprises the steps of:
    a. exposing the sample to an electrical gradient so as to separate the component in such a way that spectrin breakdown products are separated from spectrin;
    b. staining a separated product with a stain which visualizes the product;
    c. determining the presence of stain binding to the separated spectrum breakdown provided, wherein the presence of the stain indicates the presence of spectrin breakdown products.

14. The method of claim 1, wherein the detection occurs prior to manifestation of symptoms from the cellular death or degradation.

15. A method of detecting cellular death or degradation in a subject, comprising:
    obtaining a biological sample from the subject,
    determining the total amount of spectrin, including intact spectrin breakdown products, in the sample;
    determining a basal quantity of the total amount of spectrin; and
    comparing the determined quantity of the total amount of spectrin to the basal quantity of the total amount of spectrin;
wherein a quantity of the total amount of spectrin in the sample greater than the basal quantity indicates cellular death or degradation in the tissues from which the sample is taken or in tissues in fluid communication with the sample.

16. The method of claim 15, wherein the steps of determining the total amount of spectrin and the basal quantity of the total amount of spectrin are determined by measuring total spectrin immunoreactivity.

17. The method of claim 15, wherein the basal quantity of the total amount of spectrin is the quantity of the total amount of spectrin in a biological sample from a normal subject.

18. The method of claim 17, wherein the quantity of the total amount of spectrin in a biological sample from a normal subject is a substantially undetectable quantity of spectrin, when determined by the method used in the step of determining the total amount of spectrin.

19. The method of claim 17, wherein the sample is cerebrospinal fluid.

20. The method of claim 15, wherein the sample is a tissue sample.

21. The method of claim 20, wherein the sample is a neural tissue homogenate sample.

22. The method of claim 15, wherein the sample is blood or a component of blood.

23. The method of claim 15, wherein the subject is a mammal.

24. The method of claim 15, wherein the steps of determining the total amount of spectrin and the basal quantity of the total amount of spectrin are determined by an ELISA assay.

25. The method of claim 15, wherein the steps of determining the total amount of spectrin and the basal quantity of the total amount of spectrin comprise:
staining a gel obtained after exposure of the sample to electrophoresis; and
determining the amount of stain bound to intact spectrin or spectrin breakdown products.

26. The method of claim 15, wherein the cellular death or degradation is due to a condition selected from the group consisting of subarachnoid hemorrhage, stroke, multiple infarction dementia, human immunodeficiency virus (HIV)-induced neuropathy, Alzheimer's Disease, Parkinson's, muscular dystrophy, intravascular hemorrhage and Pick's Disease.

27. The method of claim 16, wherein the steps of determining the total amount of spectrin and the basal quantity of the total amount of spectrin are determined by Western Blot assay.

28. A method of preparing antibodies specific to occult epitopes of spectrin comprising:
treating spectrin so that it substantially denatures;
immunizing a mammal with the treated spectrin; and
obtaining serum from said mammal.

29. The method of claim 28, wherein said step of treating spectrin comprises treatment with an agent selected from the group consisting of: detergents, agents which produce an acidic or basic pH, chaotropic agents and organic solvents of lowered dielectric constant.

30. A method of evaluating the presence of spectrin breakdown in a mammal, comprising:
obtaining a biological sample from said mammal;
exposing said sample with an antibody specific to occult epitopes of spectrin; and
determining the amount of antibody bound to said sample.

31. A method of detecting cellular death or degradation in a subject, comprising:
obtaining a biological sample from the subject;
analyzing the sample for the presence of spectrin breakdown products by exposing the sample to an antibody specific to occult epitopes of spectrin and determining the amount of the antibody bound to the sample;
determining a basal level of spectrin breakdown products;
comparing the quantity of spectrin breakdown products determined in the analyzing step to the basal quantity of spectrin breakdown products, wherein a level of spectrin breakdown products in the sample greater than the basal level indicates cellular death or degradation in the tissues from which the sample is taken or in tissues in fluid communication with the sample.

32. A method of enriching a biological sample for spectrin breakdown products relative to intact spectrin in a biological sample, comprising precipitating intact spectrin in said sample, leaving spectrin breakdown products in solution in said sample by altering conditions which differentially affect the solubility of the intact spectrin molecule and the spectrin breakdown products; and removing the precipitated intact spectrin.

33. The method of claim 32, wherein the step of precipitating intact spectrin comprises altering the pH or ionic strength of the biological sample solution.

34. The method of claim 33, wherein said step of precipitating intact spectrin produces an enrichment of at least ten fold over the starting biological sample.

35. A method of detecting cellular death or degradation in a subject, comprising:
obtaining a biological sample from the subject;
precipitating intact spectrin in the sample, leaving spectrin breakdown products in solution in the sample by altering conditions which differentially affect the solubility of the intact spectrin molecule and the spectrin breakdown products;
removing the precipitated intact spectrin;
analyzing the resulting solution for the presence of spectrin breakdown products;
determining a basal level of spectrin breakdown products; and
comparing the quantity of spectrin breakdown products determined in the analyzing step to the basal quantity of spectrin breakdown products, wherein a level of spectrin breakdown products in the sample greater than the basal level indicates cellular death or degradation in the tissues from which the sample is taken on in tissues in fluid communication with the sample.

* * * * *

UNITED STATES PATENT AND TRADEMARK OFFICE
CERTIFICATE OF CORRECTION

PATENT NO. : 5,118,606
DATED : June 2, 1992
INVENTOR(S) : Lynch et al

It is certified that error appears in the above-indentified patent and that said Letters Patent is hereby corrected as shown below:

Column 17, line 51, after "breakdown" delete "product indicated" and replace with --products indicates--.

Column 18, line 44, after "breakdown" delete "provided" and replace with --products--.

Column 19, line 54, after "dielectric" delete "constant".

Column 20, line 56, after "taken" delete "on" and replace with --or--.

Signed and Sealed this

Twenty-sixth Day of October, 1993

Attest:

BRUCE LEHMAN

Attesting Officer

Commissioner of Patents and Trademarks